(12) United States Patent
Sawyer et al.

(10) Patent No.: US 8,377,023 B2
(45) Date of Patent: Feb. 19, 2013

(54) ABSORBENT GARMENTS WITH TAILORED STRETCH PROPERTIES IN THE LATERAL DIRECTION

(75) Inventors: Lawrence Howell Sawyer, Neenah, WI (US); Robert Lee Popp, Hortonville, WI (US); Christopher Peter Olson, Neenah, WI (US); James Marcus Carr, Kaukauna, WI (US); Mark Michael Mleziva, Appleton, WI (US); Michael John Faulks, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1478 days.

(21) Appl. No.: 10/881,718

(22) Filed: Jun. 30, 2004

(65) Prior Publication Data

US 2006/0004342 A1 Jan. 5, 2006

(51) Int. Cl.
*A61F 13/15* (2006.01)
(52) U.S. Cl. ............ 604/385.22; 604/385.29; 604/385.3
(58) Field of Classification Search ............. 604/385.22, 604/385.29–385.31
See application file for complete search history.

(56) References Cited

U.S. PATENT DOCUMENTS

| | | | |
|---|---|---|---|
| 2,931,361 A | 4/1960 | Sostrin | |
| 3,849,241 A | 11/1974 | Butin et al. | |
| 3,921,638 A | 11/1975 | Schaar | |
| 3,978,861 A | 9/1976 | Schaar | |
| 4,036,233 A | 7/1977 | Kozak | |
| 4,050,462 A | 9/1977 | Woon et al. | |
| 4,100,324 A | 7/1978 | Anderson et al. | |
| 4,205,679 A | 6/1980 | Repke et al. | |
| 4,522,874 A | 6/1985 | Pommez | |
| 4,560,372 A | 12/1985 | Pieniak | |
| 4,573,986 A | 3/1986 | Minetola et al. | |

(Continued)

FOREIGN PATENT DOCUMENTS

| EP | 0556749 A1 | 8/1993 |
|---|---|---|
| EP | 0957868 B1 | 11/1999 |

(Continued)

OTHER PUBLICATIONS

"Polyethylene—Low Density (LDPE)—Material Information," Internet web page "http://www.goodfellow.com/csp/active/STATIC/E/Polyethylene_-_Low_Density.HTML", p. 3, line 1, Goodfellow Corporation, Devon, PA.

(Continued)

*Primary Examiner* — Lynne Anderson
(74) *Attorney, Agent, or Firm* — Dority & Manning, P.A.

(57) ABSTRACT

Absorbent articles with carefully controlled stretch properties are disclosed. In particular, the absorbent articles have a percentage of stretch in the lateral direction at the widest portion in the front region of the article and/or in the back region in the range of from about 25% to about 150%. Additionally, at least about 70% of the above stretch resides in a first edge zone and in a second edge zone of the chassis. The first edge zone and the second edge zone are separated by a middle zone. The middle zone, which has the same length as each edge zone, is stretchable, but to a lesser extent than the edge zones. Through this construction, the absorbent article exhibits improved fit and appearance. Of particular advantage, the carefully controlled stretch properties prevent sagging or drooping of the crotch region, even after the crotch region has been wetted.

45 Claims, 9 Drawing Sheets

U.S. PATENT DOCUMENTS

| | | |
|---|---|---|
| 4,657,802 A | 4/1987 | Morman |
| 4,663,220 A | 5/1987 | Wisneski et al. |
| 4,704,114 A | 11/1987 | Wilson et al. |
| 4,704,116 A | 11/1987 | Enloe |
| 4,710,187 A | 12/1987 | Boland et al. |
| 4,720,415 A | 1/1988 | Vander Wielen et al. |
| 4,731,066 A | 3/1988 | Korpman |
| 4,747,846 A | 5/1988 | Boland et al. |
| 4,752,349 A | 6/1988 | Gebel |
| 4,753,646 A | 6/1988 | Enloe |
| 4,756,709 A | 7/1988 | Stevens |
| 4,808,176 A | 2/1989 | Kielpikowski |
| 4,834,736 A | 5/1989 | Boland et al. |
| 4,846,823 A | 7/1989 | Enloe |
| 4,854,995 A | 8/1989 | Kasper et al. |
| 4,865,597 A | 9/1989 | Mason, Jr. et al. |
| 4,874,451 A | 10/1989 | Boger et al. |
| 4,892,536 A | 1/1990 | DesMarais et al. |
| 4,935,021 A | 6/1990 | Huffman et al. |
| 4,938,755 A | 7/1990 | Foreman |
| 4,940,464 A | 7/1990 | Van Gompel et al. |
| 4,990,147 A | 2/1991 | Freeland |
| 5,026,364 A | 6/1991 | Robertson |
| 5,037,416 A | 8/1991 | Allen et al. |
| 5,046,272 A | 9/1991 | Vogt et al. |
| 5,104,116 A | 4/1992 | Pohjola |
| 5,114,781 A | 5/1992 | Morman |
| 5,116,662 A | 5/1992 | Morman |
| 5,151,092 A | 9/1992 | Buell et al. |
| 5,224,405 A | 7/1993 | Pohjola |
| 5,226,992 A | 7/1993 | Morman |
| 5,256,405 A | 10/1993 | Chappell et al. |
| 5,269,775 A | 12/1993 | Freeland et al. |
| 5,284,703 A | 2/1994 | Everhart et al. |
| 5,340,424 A | 8/1994 | Matsushita |
| 5,350,624 A | 9/1994 | Georger et al. |
| 5,368,584 A | 11/1994 | Clear et al. |
| 5,397,316 A | 3/1995 | LaVon et al. |
| 5,397,317 A | 3/1995 | Thomas |
| 5,455,992 A | 10/1995 | Kurschatke et al. |
| 5,486,166 A | 1/1996 | Bishop et al. |
| 5,490,846 A | 2/1996 | Ellis et al. |
| 5,503,076 A | 4/1996 | Yeo |
| 5,554,143 A | 9/1996 | Roe et al. |
| 5,593,401 A | 1/1997 | Sosalla et al. |
| 5,611,790 A | 3/1997 | Osborn, III et al. |
| 5,624,422 A | 4/1997 | Allen |
| 5,634,916 A | 6/1997 | Lavon et al. |
| 5,643,242 A | 7/1997 | Lavon et al. |
| 5,645,542 A | 7/1997 | Anjur et al. |
| 5,658,269 A | 8/1997 | Osborn, III et al. |
| 5,690,627 A | 11/1997 | Clear et al. |
| 5,695,868 A | 12/1997 | McCormack |
| 5,766,389 A | 6/1998 | Brandon et al. |
| 5,804,021 A | 9/1998 | Abuto et al. |
| 5,817,086 A | 10/1998 | Kling |
| 5,820,973 A | 10/1998 | Dodge, II et al. |
| 5,843,056 A | 12/1998 | Good et al. |
| 5,846,232 A | 12/1998 | Serbiak et al. |
| 5,873,868 A | 2/1999 | Nakahata |
| 5,883,028 A | 3/1999 | Morman et al. |
| 5,914,184 A | 6/1999 | Morman |
| 5,928,211 A | 7/1999 | Gustafsson et al. |
| 5,947,947 A | 9/1999 | Tanzer et al. |
| 5,957,907 A | 9/1999 | Sauer |
| 5,964,743 A | 10/1999 | Abuto et al. |
| 5,997,981 A | 12/1999 | McCormack et al. |
| 6,049,915 A | 4/2000 | Malowaniec |
| 6,093,870 A | 7/2000 | Carlsson |
| 6,103,953 A | 8/2000 | Cree et al. |
| 6,120,485 A | 9/2000 | Gustafsson et al. |
| 6,129,720 A | 10/2000 | Blenke et al. |
| 6,132,411 A | 10/2000 | Huber et al. |
| 6,149,638 A | 11/2000 | Vogt et al. |
| 6,149,934 A | 11/2000 | Krzysik et al. |
| 6,160,197 A | 12/2000 | Lassen et al. |
| 6,174,303 B1 | 1/2001 | Suprise et al. |
| 6,193,701 B1 | 2/2001 | Van Gompel et al. |
| 6,217,563 B1 | 4/2001 | Van Gompel et al. |
| 6,231,557 B1 | 5/2001 | Krautkramer et al. |
| 6,262,331 B1 | 7/2001 | Nakahata et al. |
| 6,264,639 B1 | 7/2001 | Sauer |
| 6,264,641 B1 | 7/2001 | Van Gompel et al. |
| 6,312,786 B1 | 11/2001 | Schwinn |
| 6,362,389 B1 | 3/2002 | McDowall et al. |
| 6,383,431 B1 | 5/2002 | Dobrin et al. |
| 6,409,711 B1 | 6/2002 | Jönbrink |
| 6,413,247 B1 | 7/2002 | Carlucci et al. |
| 6,461,338 B1 | 10/2002 | Shimoe et al. |
| 6,482,191 B1 | 11/2002 | Roe et al. |
| 6,521,811 B1 | 2/2003 | Lassen et al. |
| 6,552,245 B1 | 4/2003 | Roessler et al. |
| 6,570,056 B1 | 5/2003 | Tanzer et al. |
| 6,572,598 B1 | 6/2003 | Ashton et al. |
| 6,582,414 B1 | 6/2003 | Richardson |
| 6,595,975 B2 | 7/2003 | Vogt et al. |
| 6,610,383 B1 | 8/2003 | Morman et al. |
| 6,623,465 B1 | 9/2003 | Roe et al. |
| 6,632,212 B1 | 10/2003 | Morman et al. |
| 6,641,568 B2 | 11/2003 | Ashton et al. |
| 6,645,190 B1 | 11/2003 | Olson et al. |
| 6,679,869 B1 | 1/2004 | Schlinz et al. |
| 6,682,512 B2 | 1/2004 | Uitenbroek et al. |
| 6,702,799 B2 | 3/2004 | Otsubo |
| 6,702,800 B1 | 3/2004 | Vukos et al. |
| 6,703,538 B2 | 3/2004 | Lassen et al. |
| 6,706,028 B2 | 3/2004 | Roe et al. |
| 6,755,808 B2 | 6/2004 | Balogh et al. |
| 6,969,378 B1 | 11/2005 | Vukos et al. |
| 7,011,653 B2 | 3/2006 | Imsangjan et al. |
| 2002/0058922 A1 | 5/2002 | Skog |
| 2002/0099352 A1 | 7/2002 | Heden et al. |
| 2002/0104608 A1 | 8/2002 | Welch et al. |
| 2002/0165516 A1* | 11/2002 | Datta et al. ............... 604/385.16 |
| 2003/0023213 A1 | 1/2003 | Fernfors et al. |
| 2003/0125696 A1 | 7/2003 | Morman et al. |
| 2003/0208171 A1 | 11/2003 | Zehner et al. |
| 2004/0013850 A1 | 1/2004 | Kling |
| 2004/0044323 A1 | 3/2004 | Roessler et al. |
| 2004/0102749 A1 | 5/2004 | Olson et al. |
| 2004/0127878 A1 | 7/2004 | Olson et al. |
| 2004/0127881 A1 | 7/2004 | Stevens et al. |
| 2006/0035055 A1 | 2/2006 | Schneider et al. |

FOREIGN PATENT DOCUMENTS

| | | |
|---|---|---|
| GB | 2284538 A | 6/1995 |
| GB | 2305610 A | 4/1997 |
| GB | 2310606 A | 9/1997 |
| GB | 2325146 A | 11/1998 |
| WO | WO 9306805 A1 | 4/1993 |
| WO | WO 9519753 A1 | 7/1995 |
| WO | WO 9852506 A1 | 11/1998 |
| WO | WO 0037009 A2 | 6/2000 |
| WO | WO 0037009 A3 | 6/2000 |
| WO | WO 0115645 | 3/2001 |
| WO | WO 0234184 A1 | 5/2002 |
| WO | WO 03057106 A1 | 7/2003 |
| WO | WO 2004020174 A1 | 3/2004 |
| WO | WO 2004108041 A1 | 12/2004 |

OTHER PUBLICATIONS

PCT Search Report and Written Opinion for PCT/US2005/014167, Aug. 1, 2005.

Search Report and Written Opinion for PCT/US2005/011052, Sep. 1, 2005.

PCT Search Report and Written Opinion for PCT/US2005/002438, Jun. 29, 2005.

Translation of Japanese Patent No. JP60194947, 8 pages, Oct. 3, 1985.

* cited by examiner

ABSORBENT GARMENTS WITH TAILORED STRETCH PROPERTIES IN THE LATERAL DIRECTION

BACKGROUND OF THE INVENTION

Absorbent articles such as diapers, training pants, incontinence garments, swim undergarments, and the like conventionally include a liquid permeable body-facing liner, a liquid impermeable outer cover, and an absorbent core. The absorbent core is typically located in between the outer cover and the liner for taking in and retaining liquids (e.g., urine) exuded by the wearer.

In some of these absorbent articles, the articles contain various elastic materials to permit some expansion of the article when necessary to provide a better fit on the wearer. The elastic members are also designed to contract when being worn in order to provide the article with form-fitting properties at least in some areas. During use, the article is subjected to forces such as those generated by loading of the absorbent article and movement of the wearer. In some instances, after the absorbent article has been insulted with a liquid, the crotch area of the article may begin to droop or sag.

In this regard, improvements are needed in constructing absorbent articles that have form-fitting properties, even after the article has absorbed substantial amounts of liquid. In particular, a need exists for an absorbent article that does not droop or sag in the crotch area after being wetted. A need also exists for an absorbent article that has improved donning characteristics.

SUMMARY OF THE INVENTION

In general, the present invention relates to disposable absorbent articles having carefully controlled stretch properties. For instance, the absorbent articles may have form-fitting properties resulting in an improved fit and appearance. The carefully controlled stretch properties of the articles prevent against sagging or drooping in the crotch region, even after the article has been wetted. Specifically, the crotch region is maintained in close contact with the body during use.

For example, in one embodiment, the present invention is directed to an absorbent article comprising an outer cover. The outer cover may be stretchable and elastic and may comprise an elastic material. A stretchable bodyside liner is joined to the outer cover in a superimposed relation. The liner may be elastic in some applications.

An absorbent structure is positioned in between the outer cover and the liner. The outer cover, liner and absorbent structure form a chassis. The chassis includes a front region and a back region that define a waist opening therebetween opposite two leg openings when worn about a wearer. The chassis further includes a crotch region positioned between the two leg openings. In various embodiments, elastic members or other panels may be adhered to the chassis for forming the absorbent article.

In accordance with the present invention, the chassis comprises three equal distant zones in a lateral direction along the widest portion of the front region of the chassis and/or along the widest portion of the back region of the chassis. The zones along the front region and the back region include a first edge zone, a middle zone, and a second edge zone. The chassis is constructed such that the widest portion of the front region and/or the back region has a total stretch of from about 25% to about 150% when under a tension of 100 g/cm. The chassis is also constructed such that at least about 70%, such as at least about 80% of the above stretch is contained in the first and second edge zones. For instance, in one embodiment, at least about 90% of the total stretch present along the widest portion of the front region and at least about 90% of the total stretch present along the widest portion of the back region are contained in the respective first and second edge zones. By carefully controlling the stretch properties as described above, the present inventors have found that the article assumes better form-fitting properties and donning characteristics.

The absorbent structure that is located between the outer cover and the liner is generally positioned within the middle zone of the chassis, at least in the crotch region. In some embodiments, the absorbent structure may also extend into the first and second edge zones in the front region and/or in the back region. In one embodiment, the absorbent structure may be used in order to control the stretch properties of the chassis in the lateral direction. For instance, the absorbent structure may be attached to the liner, to the outer cover, or to both the liner and the outer cover within the middle zone. Attaching the absorbent structure to the liner and/or the outer cover may inhibit stretch of the liner and outer cover in the zones where the absorbent structure is attached, especially if the absorbent structure is less stretchable than the liner and/or the outer cover.

The absorbent structure may be attached to the liner and/or the outer cover using various methods. For instance, in one embodiment, the absorbent structure may be adhered to the liner and/or the outer cover using an adhesive, such as a hot melt adhesive. In other embodiments, ultrasonic bonding, thermal bonding, heat crimping and the like may be used. In still another embodiment, an attachment mechanism may be used to attach the absorbent structure to the liner and/or the outer cover. For instance, in one embodiment, a hook and loop fastening system may be used.

In an alternative embodiment, instead of the absorbent structure being used to control the stretch properties of the chassis, an additional component may be incorporated into the chassis that is attached to the outer cover, inner liner and/or absorbent structure in order to control stretch. For example, the additional component may be attached to the outer cover and/or the inner liner in the middle zone for inhibiting stretch in the middle zone while allowing greater stretch to occur in the edge zones. The additional component may comprise, for instance, a fabric layer or laminate that is less stretchable than the other components.

In one particular embodiment of the present invention, the chassis may be constructed such that only the first edge zone and the second edge zone have stretch properties at lower tensions. At greater tensions in the lateral direction, however, the middle zone may be stretchable. For instance, in this embodiment, the middle zone may be stretchable only at tensions greater than about 80 g/cm. In this embodiment, for instance, the absorbent structure may be adhered to the chassis in a manner such that the attachment degrades at higher tensions to allow for stretching in the middle zone.

In one embodiment, the outer cover and the liner are both made from elastic materials. For instance, the outer cover may be made from an elastic laminate containing a nonwoven web. In certain embodiments, the elastic laminate may be a stretch bonded laminate or a neck bonded laminate. The liner, on the other hand, may comprise a liquid permeable elastic film or a nonwoven web containing an elastic material.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
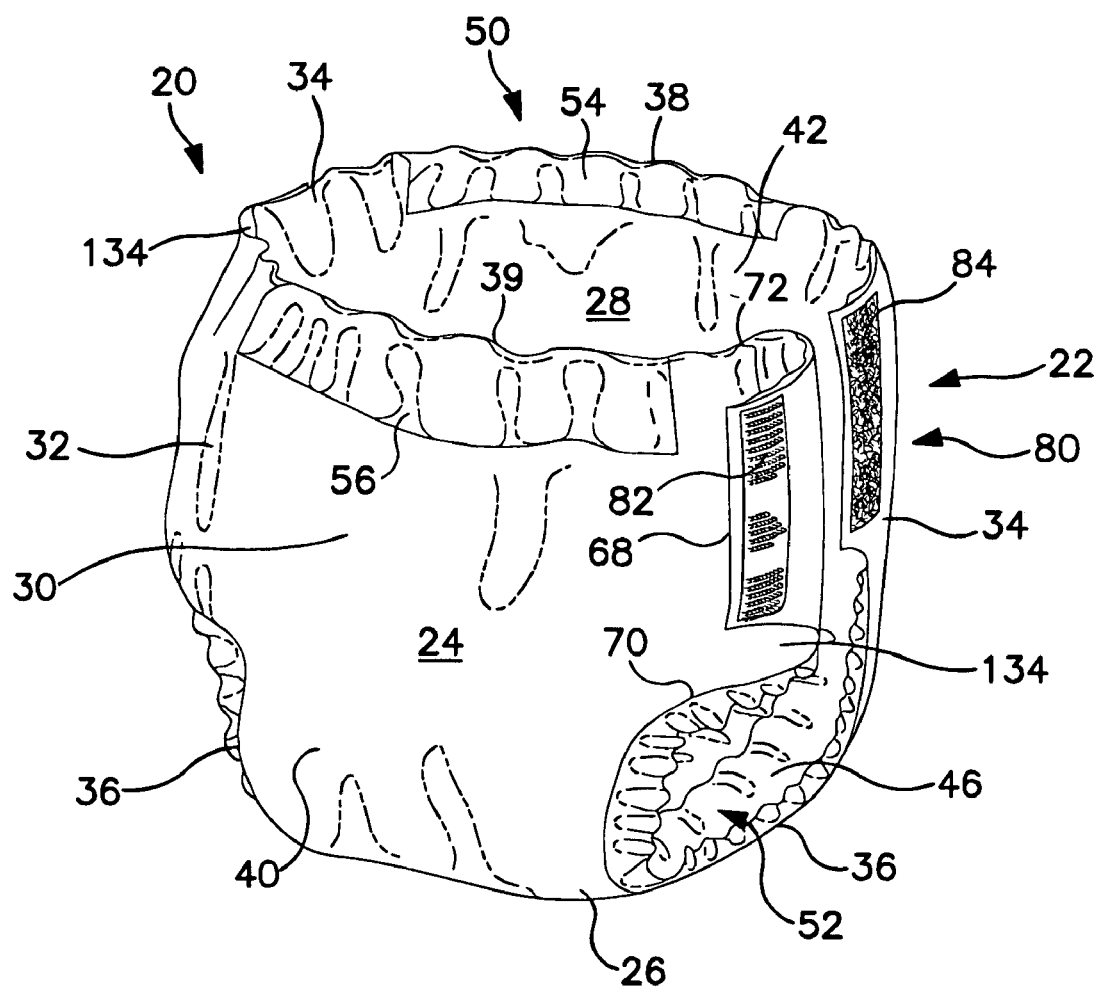
FIG. 1 is a perspective view of one embodiment of an absorbent article made in accordance with the present invention.

Repeated use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present invention.

In general, the present invention is directed to absorbent articles designed to provide improved dry and wet fit while also providing improved ease of donning. The absorbent article may be, for instance, a diaper, a toilet training pant, an adult incontinence garment, a swim pant, or the like. Absorbent garments made according to the present invention have stretch in at least one dimension and may exhibit biaxial or multi-axial stretch properties. In particular, the absorbent articles have stretch properties at least in the lateral direction of the product or, when the product is being worn, parallel to the circumference of the waist.

More particularly, absorbent articles made in accordance with the present invention may have a percentage of stretch in the lateral direction along the widest portion of the front region and/or along the widest portion of the back region in a range of from about 25% to about 150% at a tension of 100 g/cm. Additionally, at least about 70%, such as at least about 80% of the total stretch along the widest portion of the front region and/or along the widest portion of the back region resides in the edge zones of the chassis that makes up the article. More particularly, at least about 90%, such as greater than about 95% of the total stretch may originate from the edge zones. The middle zone of the chassis, on the other hand, does not substantially contribute to the stretch properties of the product. The middle zone, for instance, may contribute only minor or, at most, less than about 30% of the total stretch in the lateral direction, such as less than about 10%. In many applications, however, the middle zone should have some stretch, such as from about 2% to about 10% of the total lateral stretch.

The above stretch properties may be present along the widest portion of the front region of the chassis and/or along the widest portion of the back region of the chassis. The front region and the back region of the chassis, for instance, may both have stretch properties that fall within the above ranges. The stretch properties in the front and back regions, however, may be the same or different. Further, the stretch properties in the edge zones may be the same or different. In fact, the stretch properties within a single edge zone may be uniform across the width of the material or may vary. For example, the portion of the edge zone nearest the middle zone may have lower stretch or higher tension stretch properties than the region of the edge zone closest to the lateral edge of the product.

Absorbent articles made with the stretch properties as described above exhibit various stretch ratios along the widest portion of the front region of the article and/or along the widest portion of the back region of the article. For example, the chassis of the absorbent article may have a stretch ratio along the widest portion of either the front region or the back region that is defined by the total stretch contained in the two edge zones (EZS) versus the total stretch properties of the middle zone (MZ), which may be indicated as EZS:MZ. In particular, the stretch ratio may be less than about 19:1, such as less than about 9:1 and, in one embodiment, may be about 2.3:1.

The stretch characteristics of the front region may be the same or different than the stretch characteristics of the back region. Thus, the stretch ratio in the front region may vary widely from the stretch ratio of the back region. For example, in one embodiment, greater stretch or elasticity may be desired in the back region in order to fit more comfortably over the buttocks of a wearer.

Through the above carefully controlled stretch properties, the present inventors have found that absorbent articles exhibit improved fit and appearance. In particular, the stretch properties provide form-fitting properties while also preventing sagging or drooping of the crotch region, even after the crotch region is wetted. In particular, the construction of the absorbent article maintains the article in close contact with the body, even after the article is insulted with a liquid. The construction of the article further allows for a customized fit to a user especially in the lateral direction. Specifically, the stretch properties of the article may accommodate broader or various user shapes. The construction has also been found to facilitate donning of the product.

In general, the absorbent articles are made with stretchable and/or elastic materials. As used herein, the term "stretchable" refers to a material that may be stretchable and/or elastic (or elastomeric). That is, the material may be extended, deformed or the like, without breaking, and may or may not significantly retract after removal of an extending force. The terms "elastic" or "elastomeric" are used interchangeably herein and refer to a property of a material where upon removal of an elongating force, the material is capable of recovering to substantially its unstretched size and shape or the material exhibits a significant retractive force. The term "stretchable" refers to a property of a material where upon removal of an elongating force, the material experiences a substantially permanent deformation or the material does not exhibit a significant retractive force. In particular, elastic materials utilized in connection with the present invention may be elongated/extended or stretched in at least one direction without breaking by at least 15%, such as by at least 25% (to at least 125% of its initial unstretched length) in at least one direction, suitably by at least 50% (to at least 150% of its initial unstretched length) and which will recover, upon release of the applied stretching or biasing force, at least 10% of their elongation. It is generally advantageous that the elastomeric material or composite be capable of being elongated by at least 100%, more desirably at least 200%, of its relaxed length and recover at least 30% and more desirably 50% of its elongation upon release of a stretching, biasing force, within about one minute.

Referring to FIG. 1, for exemplary purposes, an absorbent article 20 that may be made in accordance with the present invention is shown. The absorbent article 20 may or may not be disposable, which refers to articles that are intended to be discarded after a limited period of use instead of being laundered or otherwise conditioned for reuse. It is understood that the present invention is suitable for use with various other absorbent articles intended for personal wear, including but not limited to diapers, feminine hygiene products, incontinence products, medical garments, surgical pads and bandages, other personal care or health care garments, and the like without departing from the scope of the present invention.

By way of illustration only, various materials and methods for constructing training pants such as the pants 20 of the various aspects of the present invention are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

Figure 2:
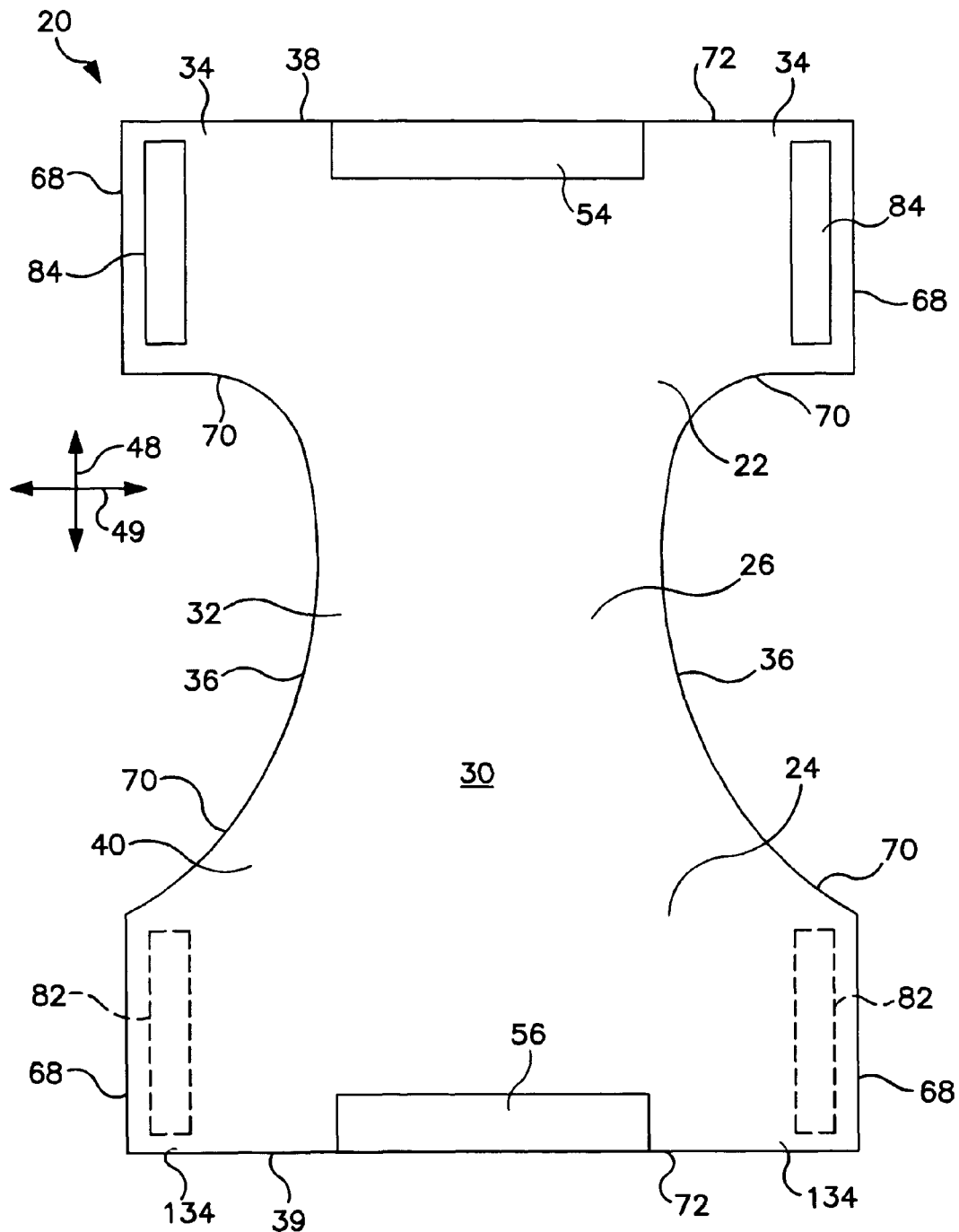
FIG. 2 is a plan view of the absorbent article shown in FIG. 1 with the article in an unfastened, unfolded and laid flat condition showing the surface of the article that faces away from the wearer.
Figure 3:
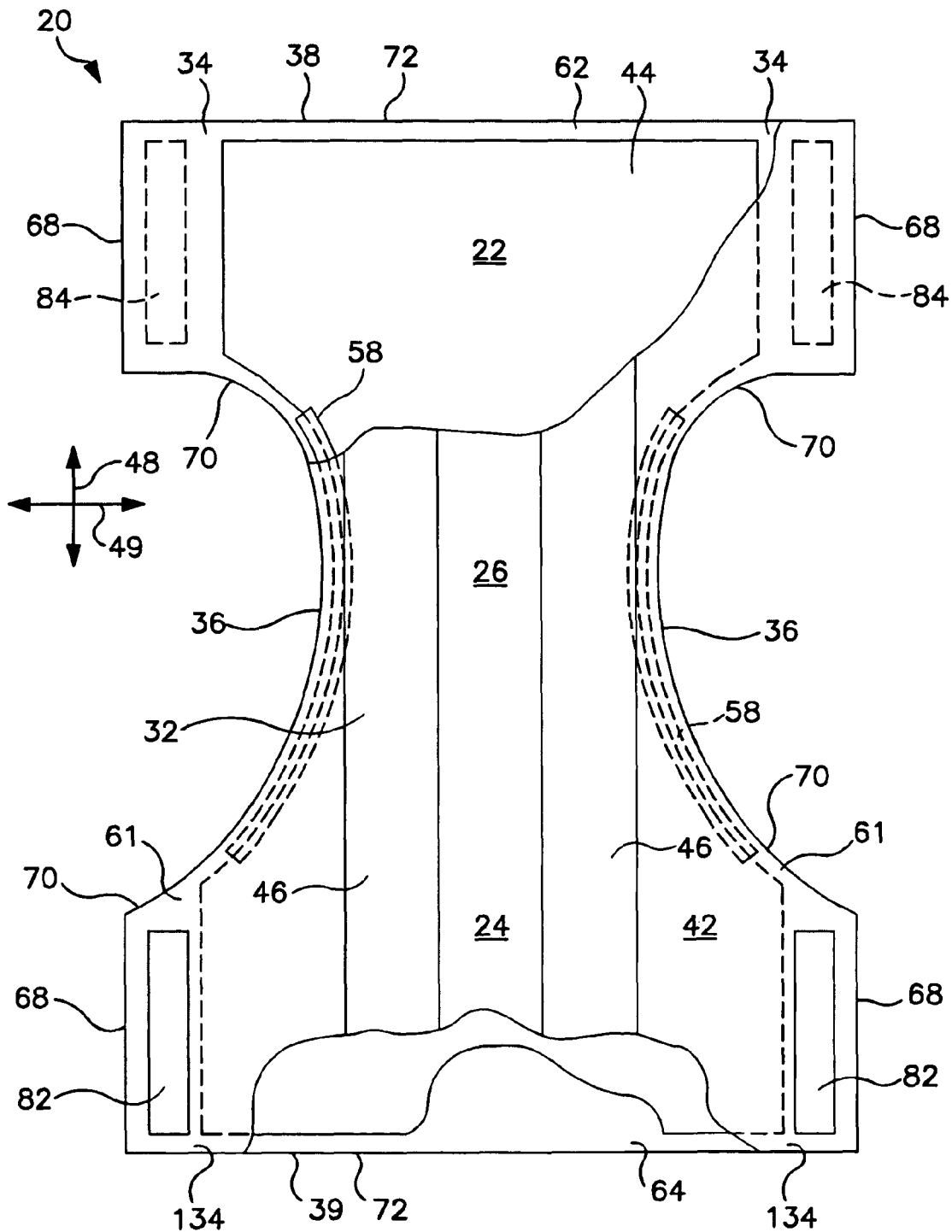
FIG. 3 is a plan view similar to FIG. 2 showing the surface of the absorbent article that faces the wearer when worn and with portions cut away to show underlying features.

A pair of training pants 20 is representatively illustrated in FIG. 1 in a partially fastened condition. The training pants 20 shown in FIG. 1 is also represented in FIGS. 2 and 3 in an opened and unfolded state. Specifically, FIG. 2 is a plan view illustrating the exterior side of the pants 20, while FIG. 3 illustrates the interior side of the pants 20. As shown in FIGS. 2 and 3, the pants 20 defines a longitudinal direction 48 that extends from the front of the training pants when worn to the back of the training pants. Opposite to the longitudinal direction 48 is a lateral direction 49.

The pants 20 includes a chassis 32 defining a pair of longitudinal end regions, otherwise referred to herein as a front region 22 and a back region 24, and a center region, otherwise referred to herein as a crotch region 26, extending longitudinally between and interconnecting the front and back regions 22, 24. The pant 20 also defines an inner surface 28 adapted in use (e.g., positioned relative to the other components of the pants 20) to be disposed toward the wearer, and an outer surface 30 opposite the inner surface. The front and back regions 22, 24 are those portions of the pants 20, which when worn, wholly or partially cover or encircle the waist or mid-lower torso of the wearer. The crotch region 26 generally is that portion of the pants 20 which, when worn, is positioned between the legs of the wearer and covers the lower torso and crotch of the wearer. The training pants 20 have a pair of laterally opposite side edges 36 and a pair of longitudinally opposite waist edges, respectively designated front waist edge 38 and back waist edge 39.

The illustrated pants 20 includes a pair of laterally opposite front side panels 34 extending laterally outward at the front region 22 and a pair of laterally opposite back side panels 134 extending laterally outward at the back region 24. The front side panels 34 and/or the back side panels 134 may be integral with the chassis 32 or may comprise separate components that are attached to the chassis as will be described in more detail hereinafter.

Referring to FIGS. 1-3, the chassis 32 includes an outer cover 40 and a bodyside liner 42 (FIGS. 1 and 3) that may be joined to the outer cover 40 in a superimposed relation therewith by adhesives, ultrasonic bonds, thermal bonds or other conventional techniques. Referring to FIG. 3, the liner 42 may suitably be joined to the outer cover 40 along the perimeter of the chassis 32 to form a front waist seam 62 and a back waist seam 64. As shown in FIG. 3, the liner 42 may suitably be joined to the outer cover 40 to form a pair of side seams 61 in the front region 22 and the back region 24. The liner 42 can be generally adapted, i.e., positioned relative to the other components of the pants 20, to be disposed toward the wearer's skin during wear of the pants. The chassis 32 may further include an absorbent structure 44 particularly shown in FIG. 3 disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates.

With the training pants 20 in the fastened position as partially illustrated in FIG. 1, the front and back side panels 34, 134 can be connected together by a fastening system 80 to define a three-dimensional pants configuration having a waist opening 50 and a pair of leg openings 52. The front and back side panels 34 and 134, upon wearing of the pants 20, thus include the portions of the training pants 20 which are positioned on the hips of the wearer. The waist edges 38 and 39 of the training pants 20 are configured to encircle the waist of the wearer and together define a waist opening 50 of the pants.

The elasticized containment flaps 46 as shown in FIG. 3 define a partially unattached edge which assumes an upright configuration in at least the crotch region 26 of the training pants 20 to form a seal against the wearer's body. The containment flaps 46 can extend longitudinally along the entire length of the chassis 32 or may extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 may also suitably include a front waist elastic member 54 (FIG. 1), a rear waist elastic member 56, and leg elastic members 58 (FIG. 3), as are known to those skilled in the art. The waist elastic members 54 and 56 can be operatively joined to the outer cover 40 and/or the bodyside liner 42 and can extend over part or all of the waist edges 38, 39. The waist elastic members 54 and 56 may comprise a single piece of elastic material or may comprise a plurality of individual components that are either connected together or spaced apart from each other. The leg elastic members 58 can be operatively joined to the outer cover 40 and/or the bodyside liner 42 and positioned in the crotch region 26 of the training pants 20.

The waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members 58 may include a plurality of dry-spun coalesced multifilament spandex elastomeric threads sold under the trade name LYCRA and available from Invista, Wilmington, Del., U.S.A.

As shown in FIGS. 1 through 3, the side panels 34 and 134 can be formed as an integral portion of the chassis 32. For example, the side panels 34, 134 can include a generally wider portion of the outer cover 40, the bodyside liner 42, and/or other components of the chassis 32. As described above, the side panels 34 and 134 may be attached together using any suitable fastening system 80.

In the embodiments shown in the figures, the side panels 34 and 134 are releaseably attachable. It should be understood, however, that in other embodiments the side panels 34 and 134 may be permanently joined together. For instance, the side panels may be made from a unitary piece of material. Alternatively, the side panels may be bonded together using ultrasonic bonding, thermal bonding or an adhesive. In this embodiment, the absorbent article is pulled over the legs when being worn.

Figure 6:
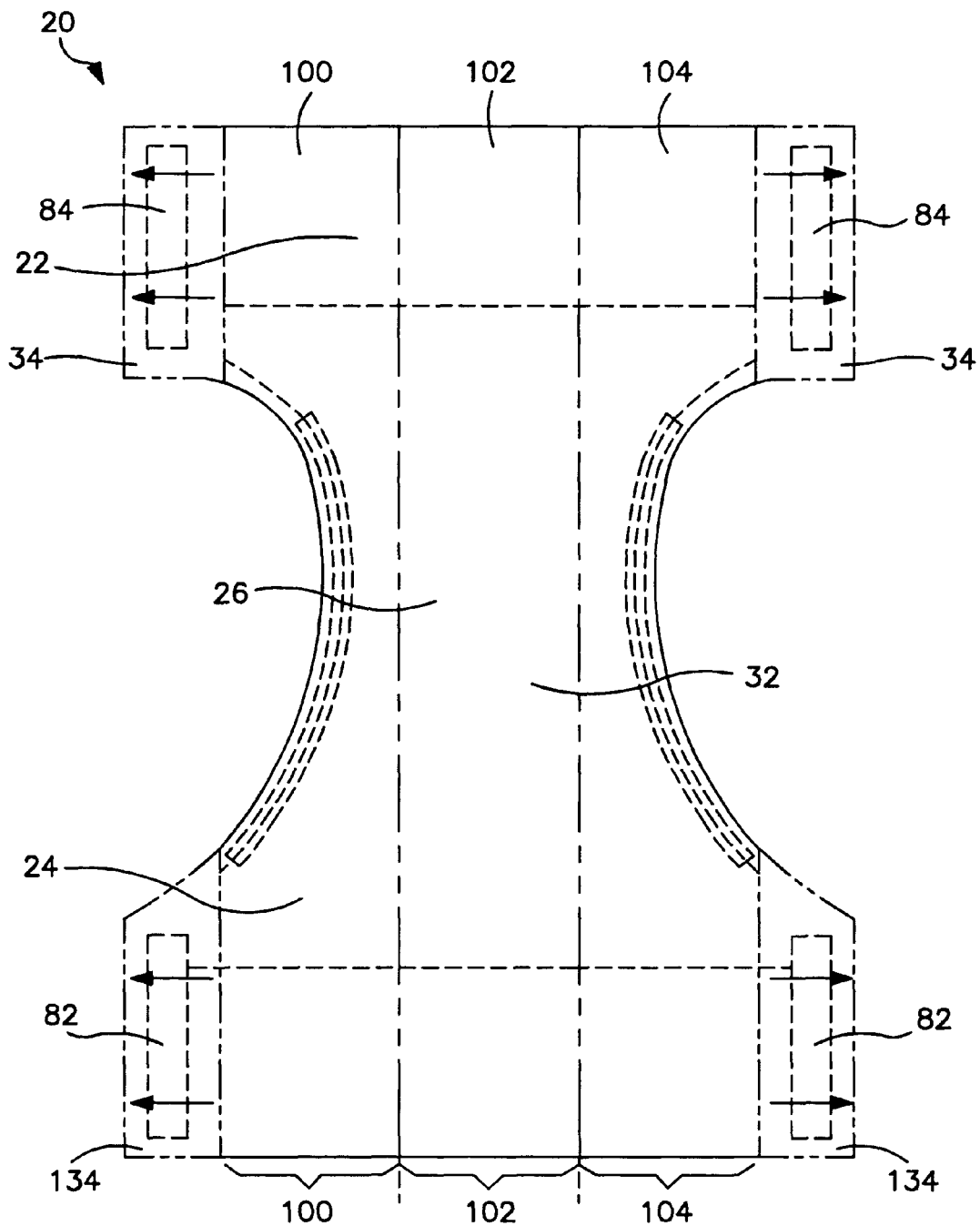
FIG. 6 is a plan view of another embodiment of an absorbent article made in accordance with the present invention showing the stretch properties of the article.

In an alternative embodiment of the present invention, the side panels 34 and 134 may be separately attached to the chassis 32 as shown in FIG. 6. For instance, the front side panels 34 can be permanently bonded to and extend transversely outward beyond the side margins of the chassis 32. Similarly, the back side panels 134 can be permanently bonded to and extend transversely outward beyond the side margins of the chassis 32 and the back region 24. The side panels 34 and 134 may be bonded to the chassis 32 using attachment means known to those skilled in the art such as adhesive, thermal or ultrasonic bonding.

The front and back side panels 34 and 134 each have a longitudinal outer edge 68, and a leg end edge 70 disposed toward the longitudinal center of the training pants 20, and waist end edges 72 disposed toward a longitudinal end of the training pants. The leg end edges 70 and the outer edges 68 of the side panels 34 and 134 form part of the pant side edges 36 of the training pants 20. The leg end edges 70 of the absorbent article 20 may be suitably curved and/or angled relative to the lateral direction 49 to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present invention. The waist end edges 72 are suitably parallel to the transverse axis 49. The waist end edges 72 of the front side panels 34 form part of the front waist edge 38 of the training pants 20, and the waist end edges 72 of the back side panels 134 form part of the back waist edge 39 of the pants.

In configurations where the side panels 34, 134 are separately attached as shown in FIG. 6, the side panels may be provided by an elastic material capable of stretching at least in a direction generally parallel to the lateral direction 49 of the training pants 20. Suitable elastic materials, as well as one process of incorporating elastic side panels into training pants, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular aspects, the elastic material may include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference to the extent that they are consistent (i.e., not in conflict) herewith. Alternatively, the side panel material may include other woven or non-woven materials, such as those described later herein as being suitable for construction of the outer cover 40 and/or the bodyside liner 42; mechanically pre-strained composites; or stretchable but inelastic materials.

The fastening system 80 may include laterally opposite first fastening components 82 adapted for refastenable engagement to corresponding second fastening components 84. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the pants 20 in its three-dimensional configuration.

The fastening components 82, 84 may be any refastenable fasteners suitable for absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include loop fasteners and the second fastening components 84 include complementary hook fasteners. Alternatively, the first fastening components 82 may include hook fasteners and the second fastening components 84 may be complementary loop fasteners. In another aspect, the fastening components 82, 84 can be interlocking similar surface fasteners, or adhesive and cohesive fastening elements such as an adhesive fastener and an adhesive-receptive landing zone or material; or the like. Although the training pants 20 illustrated in FIG. 1 indicate the back side panels 134 overlapping the front side panels 34 upon connection thereto, which is convenient, the training pants 20 can also be configured so that the front side panels 34 overlap the back side panels 134 when connected. One skilled in the art will recognize that the shape, density and polymer composition of the hooks and loops may be selected to obtain the desired level of engagement between the fastening components 82, 84. Optionally, either one or both of the fastening components 82, 84 may be provided by one of the inner or outer surfaces 28 and 30 of the side panels 34 and 134. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

Figure 4:
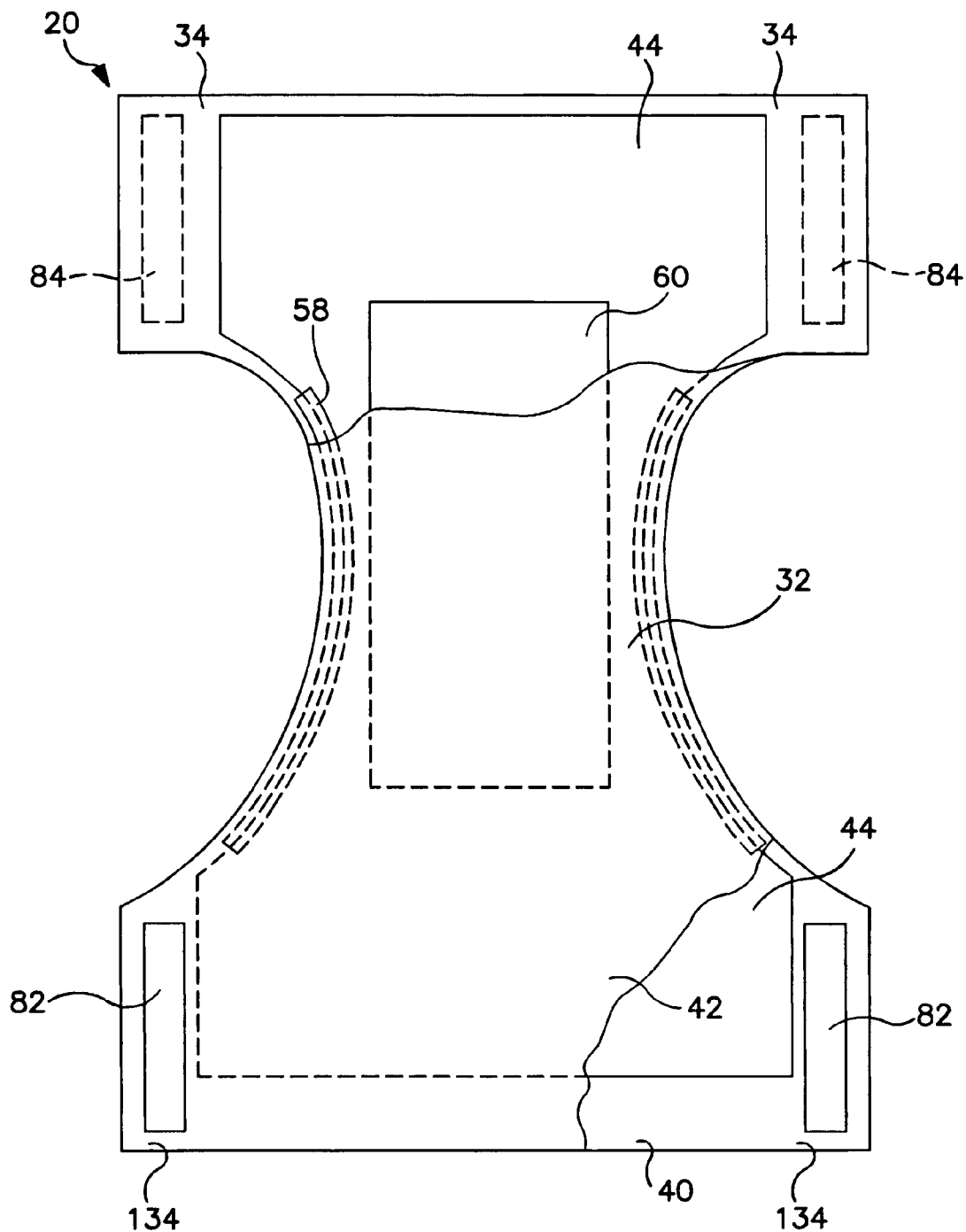
FIG. 4 is another embodiment of a plan view of an absorbent article made in accordance with the present invention showing the surface of the article that faces the wearer and with portions cut away to show underlying features.

Referring to FIG. 4, another embodiment of an absorbent article 20 made in accordance with the present invention is illustrated. In FIG. 4, the absorbent article 20 is shown in an unfolded state illustrating the interior surface of the article, which faces the wearer during use. In FIG. 4, the absorbent article 20 further includes a surge management layer 60 which may be optionally located adjacent the absorbent structure 44 and attached to various components in the article 20 such as the absorbent structure 44 or the bodyside liner 42 by methods known in the art, such as by using an adhesive. A surge management layer 60 helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. Nos. 5,486,166; and 5,490,846. Other suitable surge management materials are described in U.S. Pat. No. 5,820,973. The entire disclosures of these patents are hereby incorporated by reference herein to the extent they are consistent (i.e., not in conflict) herewith.

Figure 5:
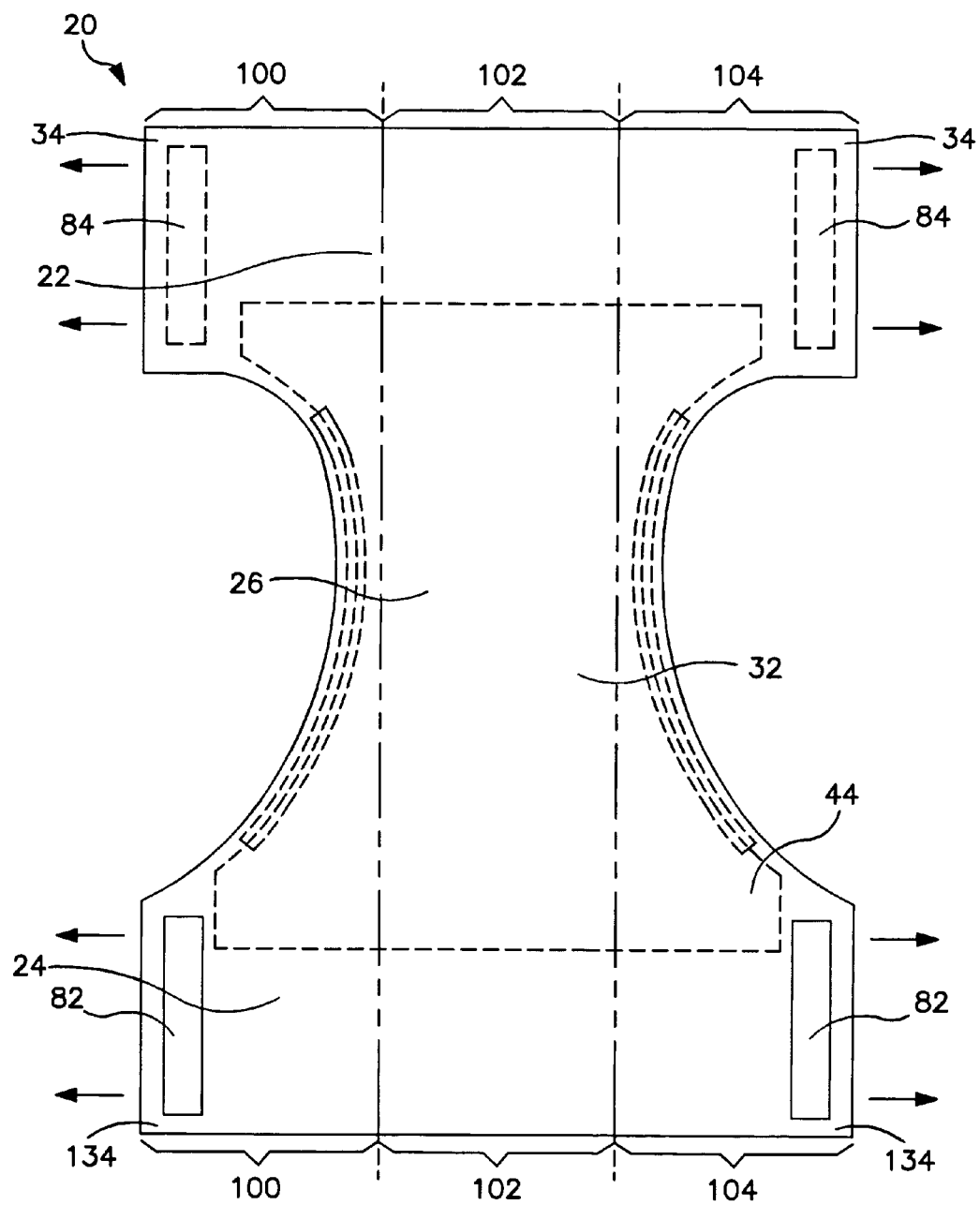
FIG. 5 is a plan view of the absorbent article shown in FIG. 4 illustrating the stretch properties of the article.

As described above, the present invention is particularly directed to absorbent articles having controlled stretch properties. For instance, referring to FIG. 5, the absorbent article 20 is shown in a flat state containing diagrammatical arrows illustrating the stretch properties of the chassis 32. In the absorbent article 20 shown in FIG. 5, not only is the chassis 32 stretchable, but the amount of stretch in the article varies in the lateral direction. For instance, as illustrated, the chassis 32 of the absorbent article 20 for purposes of explanation is partitioned into three equal distant zones. The zones include a first edge zone 100, a middle zone 102, and a second edge zone 104. The three equal distant zones are measured at the widest portion of the front region 22 of the chassis 32 and/or at the widest portion of the back region 24. In the embodiment shown in FIG. 5, the front region 22 has the same width as the back region 24.

In accordance with the present invention, the chassis 32 along the widest portion of the front region 22 and/or of the back region 24 has a total stretch of from about 25% to about 150% at a tension of 100 g/cm. For example, in some embodiments, the total stretch may be from about 30% to about 125% or from about 50% to about 100% at a tension of 100 g/cm. Most of the above total stretch in the lateral direction of the chassis resides in the first and second edge zones 100 and 104. For instance, at least about 70%, such as at least about 80% of the total stretch contained in the widest portion of the front region 22 and/or in the widest portion of the back region 24 may reside in the first edge zone 100 and the second edge zone 104. In various embodiments, for instance, at least about 90% of the total stretch, such as at least about 95% of the total stretch in the lateral direction of the chassis is maintained in the edge zones 100 and 104. Thus, less than 30% of the total stretch in the lateral direction at the widest portions of the chassis are contained in the middle zone 102.

The amount of stretch contained in the middle zone 102 may vary depending upon the particular circumstances and the desired result. In general, the middle zone 102 contains some stretch characteristics. For instance, the middle zone 102 may contain from about 2% to about 20% of the total stretch of the chassis 32 in the lateral direction, such as from about 5% to about 10% of the total stretch.

Through the above construction, the absorbent article 20 is provided with form-fitting properties that not only maximize comfort but also provide an aesthetically pleasing appearance when worn. The distribution of stretch properties, for instance, maintains the crotch region next to the wearer, even after the absorbent garment has been wetted. Further, the stretch properties facilitate donning of the article.

It should be understood that the above stretch properties of absorbent articles made in accordance with the present invention are contained solely in the chassis 32 in the lateral direction. As used herein, the stretch properties of the chassis are independent of the properties of any auxiliary components, such as flap elastics, waist elastic members, elastic gasket components, or leg elastic components.

For instance, referring to FIG. 6, when the front side panels 34 and the back side panels 134 are not integral with the chassis 32, the edge zones 100 and 104 and the middle zone 102 are measured and determined independent of the front and back side panels. As shown in FIG. 6, for instance, the chassis 32 has been divided into three equal distant zones 100, 102 and 104 that possess the stretch properties described above.

Various techniques may be used in order to produce the absorbent article 20 with the above stretch properties. In constructing absorbent articles in accordance with the present invention, for instance, the outer cover 40 may be elastic, while the bodyside liner 42 is stretchable or vice versus. In other embodiments, both the outer cover and the bodyside liner may be elastic. Depending upon the construction of the article, the absorbent structure 44 may also be stretchable and/or elastic.

In one particular embodiment, the outer cover 40 and/or the bodyside liner 42 are made from stretchable and/or elastic materials. These materials are incorporated into the absorbent article 20 in a manner that provides the article with stretch characteristics in the lateral direction. In order to inhibit stretch in the middle zone 102, a material with low stretch properties may be attached to the outer cover and/or to the liner. For instance, in one embodiment, an absorbent structure 44 is incorporated into the chassis 32 of the absorbent article 20 that has relatively low stretch properties. By attaching the absorbent structure 44 to the chassis 32 in the middle zone, stretch in this zone becomes inhibited. Because the absorbent structure 44 is not attached to the edge zones 100 or 104, however, the edge zones retain their stretch characteristics.

Figure 7:
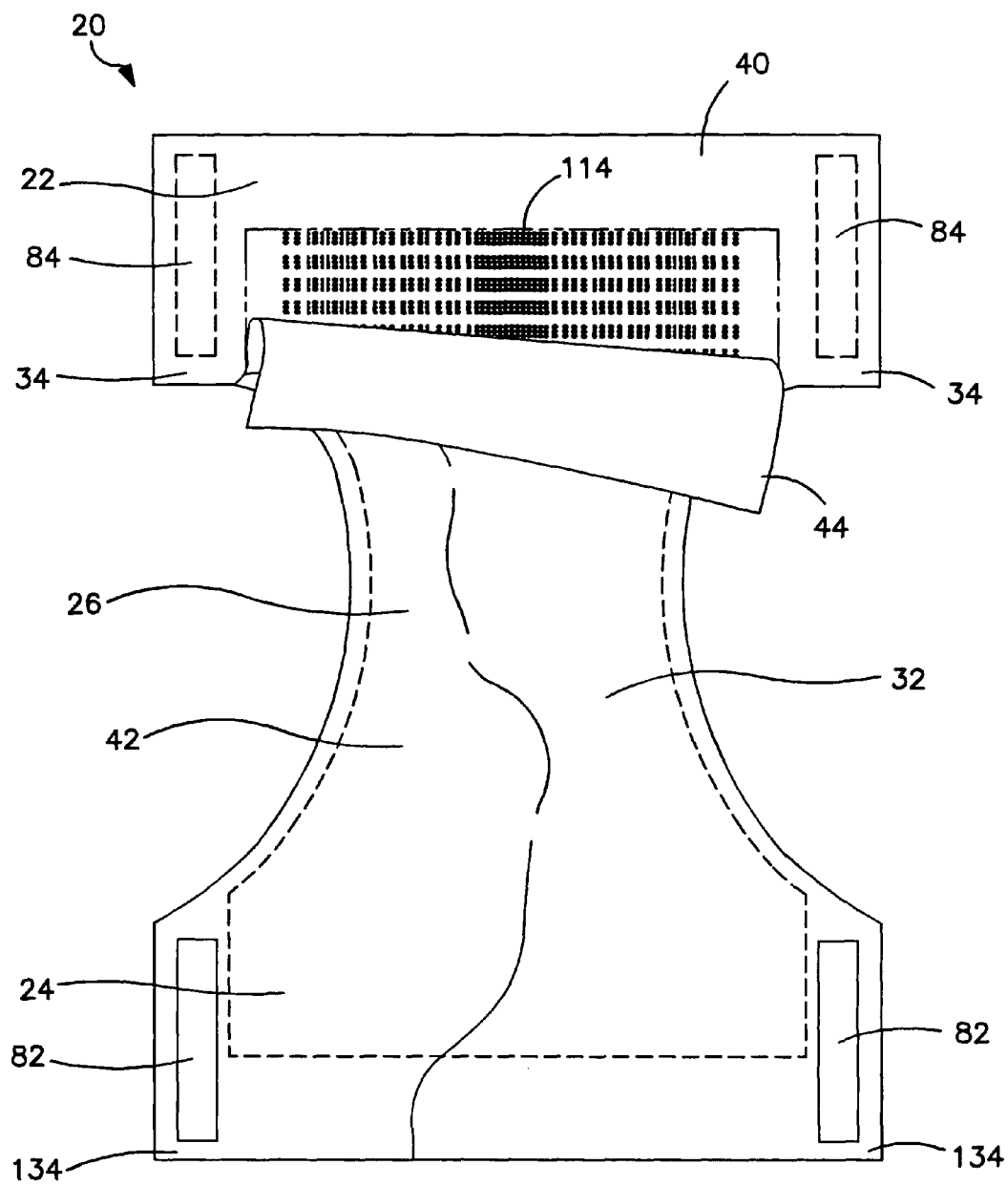
FIG. 7 is a plan view of another absorbent article made in accordance with the present invention showing the surface of the article that faces the wearer when worn and including cut away portions to show internal features.

For example, referring to FIG. 7, an absorbent article 20 made in accordance with the present invention is shown. As illustrated, the chassis 32 of the absorbent article 20 is partitioned into three equal distant zones. The absorbent article 20 includes a stretchable outer cover 40 and a stretchable liner 42. Positioned in between the outer cover 40 and the liner 42 is a substantially nonelastic absorbent structure 44. The absorbent structure 44 is shown attached to the outer cover 40 using, for instance, an adhesive 114. By attaching the absorbent structure 44 to the outer cover 40, the stretch properties of the outer cover 40 are inhibited, especially in the middle zone 102. Thus, an absorbent article 20 can be produced that not only has a total stretch of from about 25% to about 150% in the lateral direction along the widest portions of the article, but also includes a middle zone that contains less than 30% of the total stretch of the article in the lateral direction.

In accordance with the present invention, the adhesive 114 may also be applied in order to tailor the stretch properties to a particular application. For instance, as shown in FIG. 7, the adhesive 114 is applied in a pattern. In this embodiment, heavier amounts of adhesive are positioned in the middle zone while lesser amounts of adhesive are applied in the edge zones. In this manner, the middle zone 102 has less stretch properties than the edge zones 100 and 104. In fact, in one embodiment, no adhesive may be applied in all or portions of the edge zones 100 and 104. This configuration results in most of the stretch characteristics residing in the edge zones. For instance, when the chassis 32 of the absorbent article 20 is stretched in the longitudinal direction, the edge zones 100 and 104 stretch to a greater extent than the middle zone 102. As one skilled in the art may appreciate, however, the adhesive 114 may be applied in other patterns for further altering the overall stretch properties of the product.

The adhesive 114 used to construct the absorbent article 20 may be any suitable adhesive for the application. For instance, in one embodiment, a hot melt adhesive may be used. The hot melt adhesive may be, for instance, any suitable adhesive such as FINDLEY H-2096 or H-2525A adhesive commercially available from Bostik Findley Adhesives, Inc.

In addition to using an adhesive, various other attachment devices may be used in order to attach the absorbent structure 44 to the outer cover 40 and/or to the liner 42. For instance, in other embodiments, the absorbent structure may be ultrasonically bonded to the chassis 32, thermally bonded to the chassis 32, or bonded using heat crimping. In other embodiments, a mechanical attachment structure such as a hook and loop fastening system may be used in order to secure the absorbent structure to the chassis.

It should also be understood, that in addition to using the absorbent structure 44 to limit stretch within the chassis 32, other components may be incorporated into the absorbent article for the purpose of limiting stretch. For instance, in other embodiments, a nonstretchable material or a material with relatively low stretch characteristics may be incorporated into the absorbent article for the sole purpose of limiting stretch in the middle zone.

In another alternative embodiment of the present invention, the outer cover 40, the bodyside liner 42 and/or the absorbent structure 44 may be formed from multiple components and separate pieces that are attached together to form the absorbent article 20 having the desired stretch properties. In this embodiment, for instance, the outer cover 40 may be made from three separate pieces of material. Two pieces of material may be used, for instance, to construct the edge zones 100 and 104. These pieces of material may be stretchable and/or elastic. The middle zone 102 of the chassis 32, however, may be made from a material that has lower stretch properties than the material used to form the edge zones. The three pieces of material may then be connected or attached together using any suitable attachment technique, such as thermal bonding or through the use of an adhesive. In this embodiment, the outer cover, the liner or both the outer cover and the liner may be made from three separate pieces of material that assist in creating the desired stretch characteristics.

In one embodiment, the stretch contained in the middle zone 102 only becomes active when the chassis 32 is placed under higher tensions, such as tensions higher than about 80 g/cm. At lower tensions, the middle zone may only be slightly stretchable or nonstretchable. In this embodiment, the chassis 32 may be constructed by incorporating into the middle zone a material having a relatively high modulus that does not stretch until tensions reach a predetermined level.

In other embodiments, a low stretch or nonstretchable material is adhered to the outer cover 40 and/or the liner 42 to prevent stretch of the chassis 32 in the middle zone 102. The relatively low stretch material, however, may be attached to the chassis 32 in the middle zone using an attachment structure that degrades or otherwise breaks down at higher tensions. For instance, the low stretch component may be adhered to the layers of the chassis using an adhesive, pressure bonding, or thermal bonding that secures the component to the layers at lower tensions but breaks free at higher tensions releasing greater stretch in the middle zone.

As described above, the front region 22 of the chassis 32 and/or the back region 24 of the chassis 32 have a total stretch of from about 25% to about 150% in the lateral direction. It should be understood that in certain embodiments it may be desirable to have different stretch characteristics present in the front region in comparison to the stretch characteristics present in the back region. For instance, the stretch in the front region may be greater or less than the stretch in the back region. For instance, in one embodiment, the total stretch in the front region may be less than about 75% while the total stretch in the back region may be greater than about 75%. For instance, greater stretch may be needed in the back region in order to provide a better fit around the buttocks of the wearer.

The outer cover 40, the inner liner 42 and the absorbent structure 44 may be made from many different materials depending upon the particular application and the desired result. All three layers, for instance, may be stretchable and/or elastic. Further, the stretch properties of each layer may vary in order to control the overall stretch properties of the product. For instance as described above, in some embodiments the absorbent structure may be used to limit stretch of the absorbent article in the middle zone. In this embodiment, the absorbent structure may have little to no stretch properties or, at least, stretches a lesser amount than at least one of the other layers.

The outer cover 40 may be made from various materials. The outer cover 40, for instance, may be breathable and/or may be liquid impermeable. The outer cover 40 may be constructed of a single layer, multiple layers, laminates, spunbond fabrics, films, meltblown fabrics, elastic netting, microporous webs, bonded card webs or foams provided by elastomeric or polymeric materials. The outer cover 40, for instance, can be a single layer of a liquid impermeable material, or alternatively can be a multi-layered laminate structure in which at least one of the layers is liquid impermeable. In other embodiments, however, it should be understood that the outer cover may be liquid permeable. In this embodiment, for instance, the absorbent article may contain an interior liquid barrier layer.

For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Bostik Findley Adhesives, Inc., of Wauwatosa, Wis., U.S.A., or from National Starch and Chemical Company, Bridgewater, N.J. U.S.A. The liquid permeable outer layer can be any suitable material and is desirably one that provides a generally cloth-like texture. One example of such a material is a 20 gsm (grams per square meter) spunbond polypropylene nonwoven web. The outer layer may also be made of those materials of which the liquid permeable bodyside liner 42 is made.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumburg, Ill., U.S.A.

In most embodiments, the outer cover 40 is stretchable and optionally elastic. Elastic non-woven laminate webs that can be used as the outer cover 40 include a non-woven material joined to one or more gatherable non-woven webs, films, or foams. Stretch Bonded Laminates (SBL) and Neck Bonded Laminates (NBL) are examples of elastomeric composites. Non-woven fabrics are any web of material which has been formed without the use of textile weaving processes which produce a structure of individual fibers that are interconnected in an integrating manner.

Examples of suitable materials are spunbond-meltblown fabrics, spunbond-meltblown-spunbond fabrics, spunbond fabrics, or laminates of such fabrics with films, foams, or other nonwoven webs. Elastomeric materials may include cast or blown films, foams, meltblown fabrics or spunbond fabrics composed of polyethylene, polypropylene, or polyolefin elastomers, as well as combinations thereof. The elastomeric materials may include PEBAX elastomer (available from AtoChem located in Philadelphia, Pa.), HYTREL elastomeric polyester (available from Invista of Wilmington, Del.), KRATON elastomer (available from Kraton Polymers of Houston, Tex.), or strands of LYCRA elastomer (available from Invista of Wilmington, Del.), or the like, as well as combinations thereof. The outer cover 40 may include materials that have elastomeric properties through a mechanical process, printing process, heating process, or chemical treatment. For examples such materials may be apertured, creped, neck-stretched, heat activated, embossed, and microstrained; and may be in the form of films, webs, and laminates.

In particular aspects of the invention, the outer cover 40 may include a 0.4 ounces per square yard (osy) (13.6 grams per square meter (gsm)) basis weight layer of G2760 KRATON elastomer strands adhesively laminated with a 0.3 gsm layer of adhesive between two facings. Each facing can be composed of a thermal point bonded bicomponent spunbond non-woven fibrous web having a 0.7 osy (23.7 gsm) basis weight. The adhesive is similar to an adhesive which is supplied by Bostik Findley Adhesive and designated as H2525A, and the elastomer strands are placed and distributed to provide approximately 12 strands of KRATON elastomer per inch (2.54 cm) of lateral width of the outer cover 40.

Alternatively, the outer cover 40 may include a woven or non-woven fibrous web layer which has been totally or partially constructed or treated to impart the desired levels of liquid impermeability to selected regions that are adjacent or proximate the absorbent structure. For example, the outer cover 40 may include a gas-permeable, non-woven fabric layer laminated to a polymer film layer which may or may not be gas-permeable. Other examples of fibrous, cloth-like outer cover 40 materials can include a stretch thinned or stretch thermal laminate material composed of a 0.6 mil (0.015 mm) thick polypropylene blown film and a 0.7 osy (23.8 gsm) polypropylene spunbond material (2 denier fibers).

Suitable materials for a biaxially stretchable outer cover 40 include biaxially stretchable material and biaxially elastic stretchable material. One example of a suitable outer cover material can include a 0.3 osy (10.2 gsm) polypropylene spunbond that is necked 60% in the lateral direction 49 and creped 60% in the longitudinal direction 48, laminated with 3 grams per square meter (gsm) Findley 2525A styrene-isoprene-styrene based adhesive to 8 gsm PEBAX 2533 film with 20% $TiO_2$ concentrate. The outer cover 40 can suitably be stretched, laterally and/or longitudinally, by at least 30% (to at least 130% of an initial (unstretched) width and/or length of the outer cover 40). More suitably, the outer cover 40 can be stretched laterally and/or longitudinally, by at least 50% (to at least 150% of the unstretched width or length of the outer cover 40). Even more suitably, the outer cover 40 can be stretched, laterally and/or longitudinally, by at least 100% (to at least 200% of the unstretched width or length of the outer cover 40). Tension force in the outer cover 40 at 50% extension is suitably between 50 and 1000 grams, more suitably between 100 and 600 grams, as measured on a 3 inch (7.62 cm) wide piece of the outer cover material.

Another example of a suitable material for a biaxially stretchable outer cover 40 is a breathable elastic film/non-woven laminate, described in U.S. Pat. No. 5,883,028, issued to Morman et al., incorporated herein by reference to the extent that it is consistent (i.e. not in conflict) herewith. Examples of materials having two-way stretchability and retractability are disclosed in U.S. Pat. No. 5,116,662 issued to Morman and U.S. Pat. No. 5,114,781 issued to Morman, both of which are hereby incorporated herein by reference to the extent that it is consistent (i.e., not in conflict) herewith. These two patents describe composite elastic materials capable of stretching in at least two directions. The materials have at least one elastic sheet and at least one necked material, or reversibly necked material, joined to the elastic sheet at least at three locations arranged in a nonlinear configuration, so that the necked, or reversibly necked, web is gathered between at least two of those locations.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. A suitable bodyside liner 42 may be manufactured from a wide selection of web materials, such as porous foams, reticulated foams, apertured plastic films, woven and non-woven webs, or a combination of any such materials. For example, the bodyside liner 42 may include a meltblown web, a spunbonded web, or a bonded-carded-web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity.

The bodyside liner 42 may also be stretchable, and more suitably it may be elastomeric. Suitable elastomeric materials for construction of the bodyside liner 42 can include elastic strands, LYCRA elastics, cast or blown elastic films, non-woven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon of Cleveland, Ohio), or PEBAX elastomers.

As an additional example, in one aspect the bodyside liner 42 suitably includes a non-woven, spunbond polypropylene fabric composed of about 2 to 3 denier fibers formed into a web having a basis weight of about 12 gsm which is necked approximately 60 percent. Strands of about 9 gsm KRATON G2760 elastomer material placed eight strands per inch (2.54 cm) are adhered to the necked spunbond material. The fabric is surface treated with an operative amount of surfactant, such as about 0.6 percent AHCOVEL Base N62 surfactant, available from ICI Americas, a business having offices in Wilmington, Del., U.S.A. The surfactant can be applied by any conventional means, such as spraying, printing, brush coating or the like. Other suitable materials may be stretchable biaxially stretchable materials, such as a neck stretched/creped spunbond. The bodyside liner 42 can also be made from stretchable materials as are described in U.S. patent application Ser. No. 09/563,417 filed on May 3, 2000 by Roessler et al. The bodyside liner 42 can also be made from biaxially stretchable materials as are described in U.S. patent application Ser. No. 09/698,512 filed on Oct. 27, 2000 by Vukos et al.

The liner 42 can suitably be stretched, laterally and/or longitudinally, by at least 30% (to at least 130% of an initial (unstretched) width and/or length of the liner 42). More suitably, the liner 42 can be stretched laterally and/or longitudinally, by at least 50% (to at least 150% of the unstretched width or length of the liner 42). Even more suitably, the liner 42 can be stretched, laterally and/or longitudinally, by at least 100% (to at least 200% of the unstretched width or length of the liner 42). Tension force in the liner 42 at 50% extension is suitably between 50 and 1000 grams, more suitably between 100 and 600 grams, as measured on a 3 inch (7.62 cm) wide piece of the liner material.

In order to make the outer cover 40 and/or the liner 42 more stretchable or in order to otherwise control the stretch properties of the outer cover or liner, the materials may be perforated. The elastic side panels may also be perforated in order to increase the stretch characteristics. The perforations formed into the materials may be in any suitable shape, such as slits or holes.

The absorbent structure 44 may be disposed between the outer cover 40 and the bodyside liner 42. The absorbent structure 44 can be any structure or combination of components which are generally compressible, conformable, non-irritating to a wearer's skin, and capable of absorbing and retaining liquids and certain body wastes. For example, the absorbent structure 44 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular aspect, the absorbent web material is a matrix of cellulosic fluff and superabsorbent hydrogel-forming particles. The cellulosic fluff may include a blend of wood pulp fluff. One preferred type of fluff is identified with the trade designation CR 1654, available from Bowater of Greenville, S.C., USA, and is a bleached, highly absorbent sulfate wood pulp containing primarily southern soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art. Furthermore, the absorbent structure may itself encompass multiple layers in the Z direction. Such multiple layers may take advantage of differences in absorbency capacity, such as by placing a lower capacity absorbent material layer closer to the liner 42 and a higher capacity absorbent material closer to the outer cover layer 40. Likewise, discrete portions of an absorbent single-layered structure may encompass higher capacity absorbents, and other discrete portions of the structure may encompass lower capacity absorbents.

As a general rule, the superabsorbent material is present in the absorbent web in an amount of from about 0 to about 90 weight percent based on total weight of the web. The web may have a density within the range of about 0.10 to about 0.60 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and desirably is capable of absorbing more than about 25 times its weight in liquid. Suitable superabsorbent materials are readily available from various suppliers. For example, SXM 9394, and Favor 9543 superabsorbents are available from DeGussa Superabsorbers.

After being formed or cut into a desired shape, the absorbent web material may be wrapped or encompassed by a suitable tissue or meltblown web or the like wrap sheet that aids in maintaining the integrity and shape of the absorbent structure 44.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference to the extent they are consistent (i.e., not in conflict) herewith.

In a particular aspect of the absorbent article of the present invention, the absorbent structure 44 may also be elastomeric. For this purpose, the absorbent web material can include elastomeric fibers in an amount which is at least a minimum of about 2 wt %. The amount of elastomeric fibers can alternatively be at least about 3 wt %, and can optionally be at least about 5 wt % to provide improved performance. In addition, the amount of elastomeric fibers can be not more than about 60 wt %. Alternatively, the amount of elastomeric fibers can be not more than about 45 wt %, and optionally, can be not more than about 30 wt % to provide improved benefits. These values may impact the absorbent structure 44 by affecting the desired levels of stretchability and structural stability without excessively degrading the physical properties or the liquid-management properties of the absorbent structure. An absorbent web material with an excessively low proportion of elastomeric fibers may be insufficiently stretchable, and a web material with an excessively high proportion of elastomeric fibers may exhibit an excessive degradation of its absorbency functionalities, such as poor intake, poor distribution, poor retention of liquid.

The absorbent structure 44 may include an elastomeric coform absorbent web material. Such materials are described for instance in U.S. Pat. Nos. 6,231,557 B1 and 6,362,389 B1, which are each incorporated by reference herein to the extent they are consistent (i.e., not in conflict) herewith. In particular aspects, the elastomeric coform material can have an overall coform basis weight of at least about 50 gsm, such as up to about 1200 gsm. The coform basis weight, for example, may be at least about 100 gsm, such as at least about 200 gsm. These values can provide the absorbent structure with the desired stretchability and structural stability without excessively degrading the physical properties or the liquid-management functionalities of the absorbent structure. For example, retention portions having excessively low proportions of elastomeric coform material may not be sufficiently stretchable. Conversely, an absorbent web material having excessively large amounts of elastomeric coform materials can exhibit an excessive degradation of their absorbency functionalities, such as an excessive degradation of intake, distribution and/or retention properties.

Other examples of usable elastomeric absorbent bodies are described in international patent application WO 03/051254 and U.S. Pat. Nos. 5,964,743, 5,645,542, 6,231,557, and 6,362,389 B1, each of which are incorporated by reference herein to the extent they are consistent (i.e., not in conflict) herewith.

Testing Procedures

For the purposes of the present invention, the properties, such as tensile strength, tensile load and elongation, of a material or component can be determined by ASTM Procedure D 3039 "Tensile Properties of Polymer Matrix Composite Materials", with the following specifications and particulars:
Test facility environment: 23+−0.1 degree C., and relative humidity of 50+−0.2 percent;
Gauge length: 50.8 mm;
Specimen width (aligned perpendicular to the applied force): 3 inches (76.2 mm);
Jaw width (measured parallel to the applied force): ½ inch (12.7 mm);
Jaw length (measured perpendicular to the applied force): 4 inches (101.6 mm);
Jaw speed: 500 mm/min.

A suitable testing device is a SINTECH constant rate of extension tensile tester (available from MTS Systems Corporation, a business having offices located in Edens Prairie, Minn.), or an equivalent device. The tensile tester is operatively programmed with suitable software, such as TESTWORKS software (available from MTS Systems Corporation), or an equivalent software.

Test specimens may include a single component, multi-components or multi-layered structure and are stapled at their length-wise ends at locations outside of the test area to prevent slippage of the individual materials within the composite when the composite is mounted in the jaws of the testing device.

The 3-inch (76.2 mm) width of each specimen can be cut with a JDC precision cutter (available from Thwing-Albert Instrument Company, a business having offices located in Philadelphia, Pa.), or an equivalent device.

Figure 8:
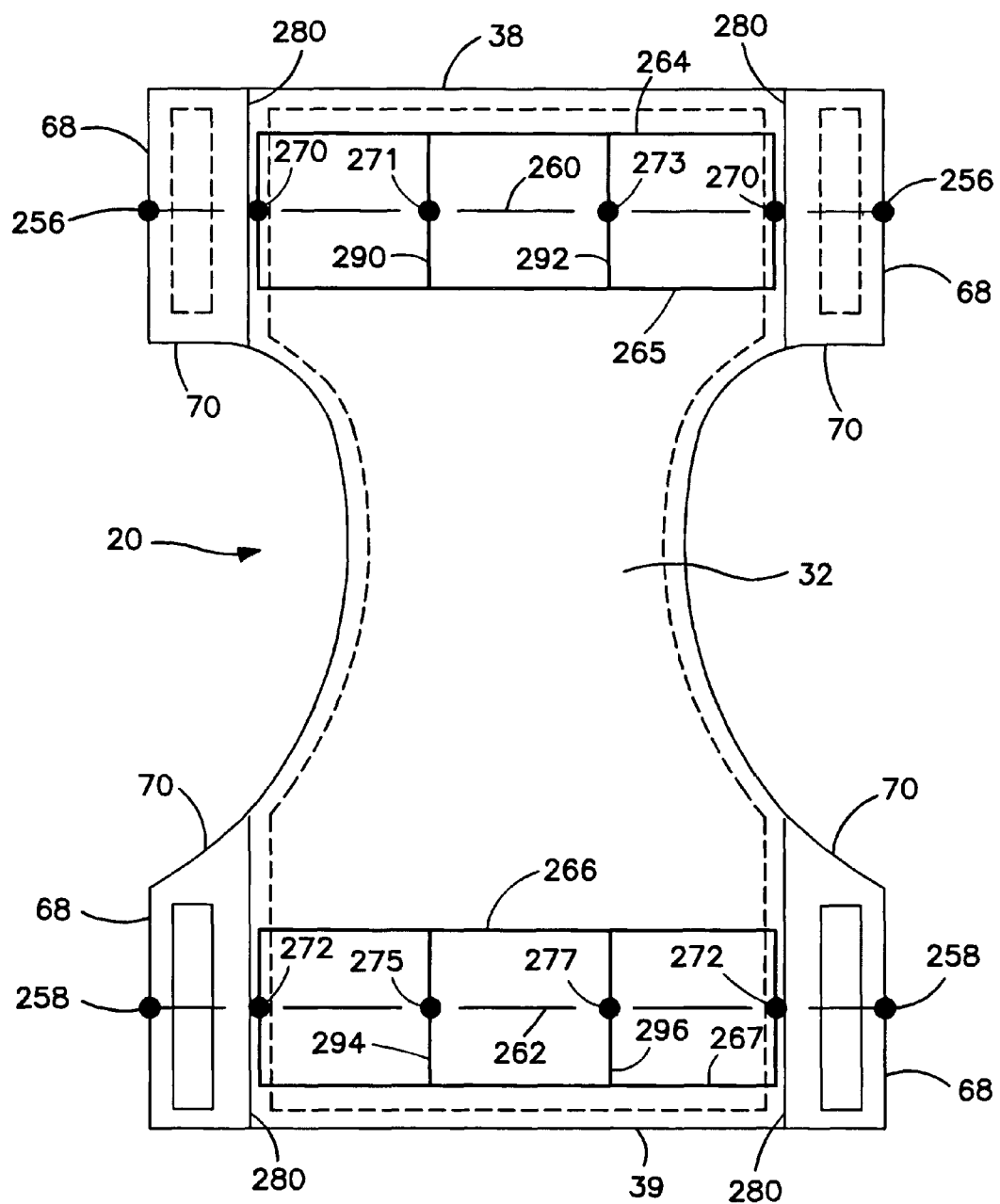
FIG. 8 is a plan view of the absorbent article shown in FIG. 3 illustrating where one might obtain a sample from the chassis in order to test for stretch characteristics and tensile strength.

Test specimens are removed from an individual absorbent article 20, each test specimen is desirably removed from the absorbent article 20 at a location which is centered along the front and back waist lateral centerlines 260 and 262, as representatively shown in FIG. 8. The specimen locations are selected to avoid the effects of auxiliary elasticized components that may be present; such as any auxiliary fastening means, side panels and the like that is subsequently attached to the chassis, elasticized waistbands, elasticized containment flaps and the like. In certain applications, any of the above described auxiliary elasticized components may be removed from the absorbent article prior to obtaining samples for testing or, alternatively, may be inactivated by cutting the auxiliary elastic components every one centimeter along the length of the component.

In the embodiment shown in FIG. 8, for instance, the samples are obtained from the absorbent article 20 independent of the front and back side panels which, in this embodiment, are not integral with the chassis 32.

Figure 9:
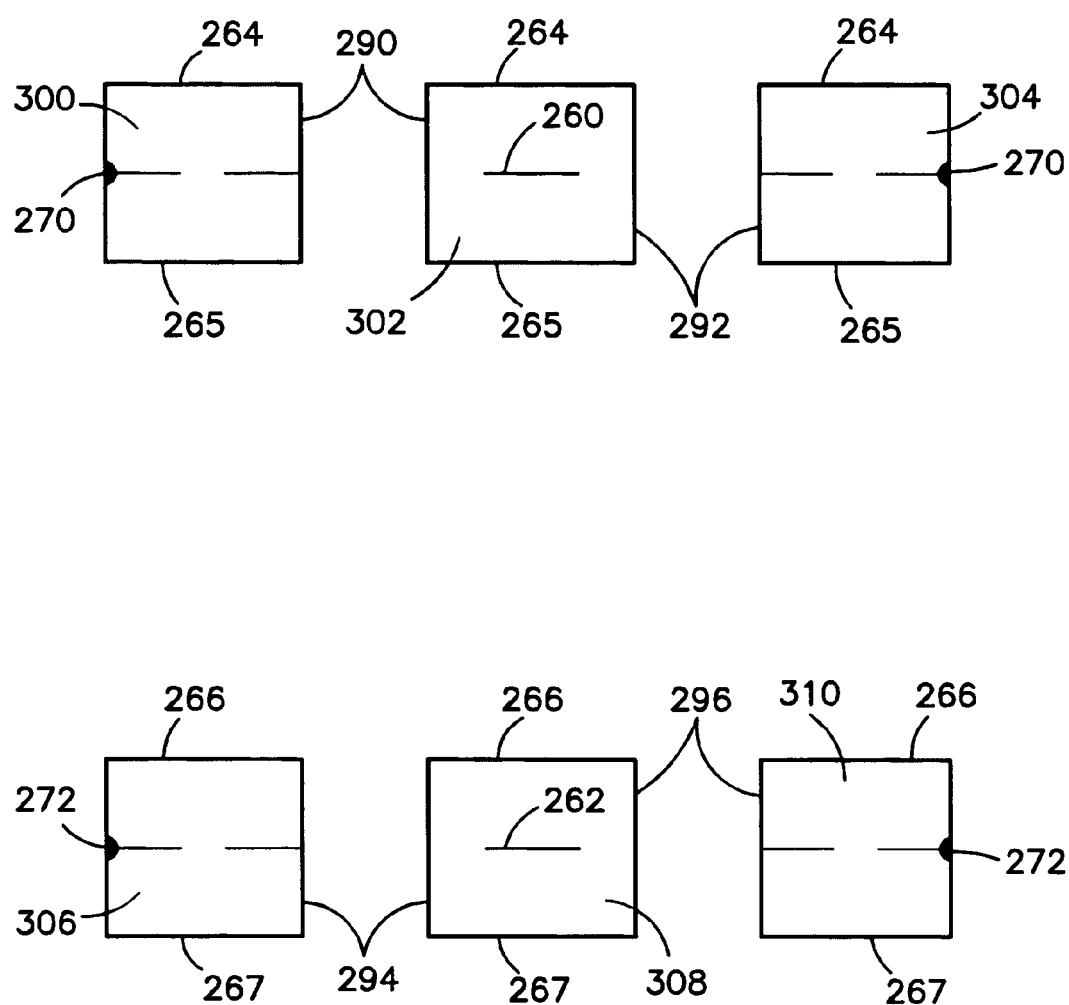
FIG. 9 is a plan view illustrating the sample obtained from the chassis shown in FIG. 8 severed into three equidistant sections for stretch testing.

As shown in FIG. 9, once the strips are obtained from an individual absorbent article, each strip is severed into three equidistant sections. The sections include a first front edge zone 300, a front middle zone 302, a second front edge zone 304, a first back edge zone 306, a back middle zone 308, and a second back edge zone 310. Each of the individual sections or zones are then tested using the above described testing device.

Three specimens are tested per sample section. More than one absorbent article may be needed in order to obtain the specimens. The reported value of the particular property being determined for each sample is the arithmetic average of the corresponding data points measured for the three specimens during the testing.

The following data point is recorded for each test specimen:
Elongation at 100 g load per centimeter width (%);
The percent elongation can be determined in accordance with the following formula:

$$\% \text{ elongation} = (L_f - L_0) * 100 / L_0;$$

where:
$L_0$=initial, non-elongated length
$L_f$=final, elongated length at 100 gram load per centimeter width Once the stretch characteristics are known for each of the six sections 300, 302, 304, 306, 308, and 310, total stretch of the front zones and/or the back zones may be calculated. The percent stretch in each section may also be determined. As described above, absorbent articles made according to the present invention have greater stretch characteristics in the first and second front edge zone 300 and 304 and/or the first and second back edge zone 306 and 310 in comparison to the front and/or back middle zones 302 and 308.

Specimen Preparation
1. The absorbent article 20 is unfastened, unfolded and laid in a relaxed, flat condition and placed on a flat surface such as that of a table or lab countertop showing the surface of the article that faces the wearer. Allow the article 20 to rest relaxed in this position for five minutes.
2. After five minutes, tape the entire edge of the front waist edge 38 of the absorbent article 20 to the underlying table or countertop using clear tape such as "Scotch" tape.
3. Stretch the absorbent article 20 taut in the longitudinal direction and tape the entire edge of the back waist edge 39 to the underlying table or countertop using clear tape such as "Scotch" tape.
4. Determine the front centerpoints 256 of each longitudinal outer edge 68. Mark the front centerpoints 256 at the point that equals the total length of each longitudinal side edge 68 divided by two.
5. Construct the front waist lateral centerline 260 by measuring the distance between each front centerpoints 256, and marking the centerline 260.
6. Determine the back centerpoints 258 of each longitudinal outer edge 68. Mark the back centerpoints 258 at the point that equals the total length of each longitudinal side edge 68 divided by two.
7. Construct the back waist lateral centerline 262 by measuring the distance between each back centerpoints 258, and marking the centerline 262.
8. Locate all auxiliary fastening means, side panels and the like that is subsequently attached to the chassis and cut at cut lines 280 and remove from the chassis.
9. Mark front centerline centerpoints 270 at the chassis edges.
10. Measure the distance between the front centerline centerpoints 270 and mathematically divide this distance by three and mark two centerpoints 271 and 273 equidistant from each other such that three equal length sample sections are generated.
11. Determine and mark the front waist area test sample lateral edges 264 and 265, ensuring the test sample area has no auxiliary components such as elasticized waistbands, elasticized containment flaps and the like. Lateral edges 264 and 265 are parallel to front lateral centerline 260.
12. Determine and mark the front waist area test sample longitudinal edges 290 and 292, using centerpoints 271 and 273, ensuring the test sample area has no auxiliary components such as elasticized waistbands, elasticized containment flaps and the like. Longitudinal edges 290 and 292 are perpendicular to lateral edges 264 and 265.
13. Mark back centerline centerpoints 272 at the chassis edges.
14. Measure the distance between the back centerline centerpoints 272 and mathematically divide this distance by three and mark two centerpoints 275 and 277 equidistant from each other such that three equal length sample sections are generated.
15. Determine and mark the back waist area test sample lateral edges 266 and 267, ensuring the test sample area has no auxiliary components such as elasticized waistbands, elasticized containment flaps and the like. Lateral edges 266 and 267 are parallel to back lateral centerline 262.
16. Determine and mark the back waist area test sample longitudinal edges 294 and 296, using centerpoints 275 and 277, ensuring the test sample area have no auxiliary components such as elasticized waistbands, elasticized containment flaps and the like. Longitudinal edges 294 and 296 are perpendicular to lateral edges 266 and 267.
17. Mark each of the six test specimens based on location and cut them away from the absorbent article as shown in FIG. 9.
18. If the six test specimens have a length that is less than 50.8 mm, the gauge length may be reduced in order to test the specimens. The gauge length should not be less than 25.4 mm.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:
1. An absorbent article comprising:
an outer cover comprising an elastic material;
a stretchable bodyside liner joined to the outer cover in a superimposed relation;
an absorbent structure positioned in between the outer cover and the liner; and
wherein the outer cover, liner and absorbent structure form a chassis, the chassis including a front region and a back region that define a waist opening therebetween opposite two leg openings when worn about a wearer, the chassis comprising three equal distant zones in a lateral direction along the widest portion of the chassis, the zones including a first edge zone, a middle zone, and a second edge zone, and wherein the chassis is constructed such that the chassis has a total stretch of from about 25% to about 150% along the widest portion at a tension of 100 g/cm and wherein at least about 70% of the above stretch is contained in the respective first and second edge zones.
2. An absorbent article as defined in claim 1, wherein at least about 80% of the total stretch is contained in the respective first and second edge zones.
3. An absorbent article as defined in claim 1, wherein at least about 90% of the total stretch is contained in the respective first and second edge zones.
4. An absorbent article as defined in claim 1, wherein at least about 2% of the total stretch is contained in the middle zone.
5. An absorbent article as defined in claim 1, wherein at least about 5% of the total stretch is contained in the middle zone.
6. An absorbent article as defined in claim 1, wherein the widest portion of the chassis is located adjacent the waist opening in the front region.
7. An absorbent article as defined in claim 1, wherein the widest portion of the chassis is located adjacent the waist opening in the back region.
8. An absorbent article as defined in claim 1, wherein the widest portion of the chassis is located either in the front region or the back region and wherein both the widest portion of the back region and the widest portion of the front region has a total stretch of from about 25% to about 150% at a tension of 100 g/cm and wherein at least about 70% of the above stretch is contained in the respective first and second edge zones.
9. An absorbent article as defined in claim 1, wherein the first edge zone has substantially the same stretch properties as the second edge zone.
10. An absorbent article as defined in claim 1, wherein the middle zone along the widest portion of the chassis is only stretchable when placed under a lateral tension of greater than about 80 g/cm.
11. An absorbent article as defined in claim 1, wherein the stretch in the middle zone is reduced by attaching the absorbent structure to the liner, the outer cover or to both the liner and the outer cover.
12. An absorbent article as defined in claim 11, wherein the absorbent structure is attached to the liner, the outer cover or to both the liner and the outer cover using an adhesive.
13. An absorbent article as defined in claim 11, wherein the absorbent structure is attached to the liner, the outer cover or to both the liner and the outer cover using an attachment mechanism.
14. An absorbent article as defined in claim 1, wherein the outer cover is elastic.
15. An absorbent article as defined in claim 14, wherein the liner is elastic.
16. An absorbent article as defined in claim 12, wherein the adhesive is applied in varying amounts in order to control stretch properties of the chassis in the lateral direction.
17. An absorbent article as defined in claim 1, wherein the outer cover comprises an elastic laminate containing a nonwoven web.
18. An absorbent article as defined in claim 1, wherein the liner comprises a liquid permeable elastic film or a nonwoven web containing an elastic material.
19. An absorbent article as defined in claim 1, wherein the outer cover and the bodyside liner are continuous from the first edge zone to the second edge zone.
20. An absorbent article comprising:
a stretchable outer cover;

a stretchable bodyside liner joined to the outer cover in a superimposed relation;

an absorbent structure positioned in between the outer cover and the liner; and wherein the outer cover, liner and absorbent structure form a chassis, the chassis including a front region and a back region that define a waist opening therebetween opposite two leg openings when worn about a wearer, the chassis comprising three equal distant zones in a lateral direction along the widest portion of the front region of the chassis and along the widest portion of the back region of the chassis, the zones in the front region and in the back region including a first edge zone, a middle zone, and a second edge zone, and wherein the chassis is constructed such that the chassis has a total stretch of from about 25% to about 150% along the widest portion of the front region and along the widest portion of the back region at a tension of 100 g/cm and wherein at least about 70% of the above stretch along the widest portion of the front region and along the widest portion of the back region is contained in the corresponding first and second edge zones.

21. An absorbent article as defined in claim 20, wherein at least about 80% of the total stretch contained along the widest portion of the front region is contained in the respective first and second edge zones and wherein at least about 80% of the total stretch contained in the widest portion of the back region is also contained in the respective first and second edge zones.

22. An absorbent article as defined in claim 20, wherein at least about 90% of the total stretch contained along the widest portion of the front region is contained in the respective first and second edge zones and wherein at least about 90% of the total stretch contained in the widest portion of the back region is also contained in the respective first and second edge zones.

23. An absorbent article as defined in claim 20, wherein at least about 2% of the total stretch of the front region is contained in the middle zone and wherein at least about 2% of the total stretch of the back region is contained in the middle zone.

24. An absorbent article as defined in claim 20, wherein at least about 5% of the total stretch of the front region is contained in the middle zone and wherein at least about 5% of the total stretch of the back region is contained in the middle zone.

25. An absorbent article as defined in claim 20, wherein the first edge zones have substantially the same stretch properties as the second edge zones.

26. An absorbent article as defined in claim 20, wherein the middle zone along the widest portion of the front region is only stretchable when placed under a lateral tension of greater than about 80 g/cm.

27. An absorbent article as defined in claim 20, wherein the stretch in the middle zone of the front region and the back region are reduced by attaching the absorbent structure to the liner, the outer cover or to both the liner and the outer cover.

28. An absorbent article as defined in claim 27, wherein the absorbent structure is attached to the liner, the outer cover or to both the liner and the outer cover using an adhesive.

29. An absorbent article as defined in claim 27, wherein the absorbent structure is attached to the liner, the outer cover or to both the liner and the outer cover using an attachment mechanism.

30. An absorbent article as defined in claim 20, wherein the outer cover is elastic.

31. An absorbent article as defined in claim 20, wherein the liner is elastic.

32. An absorbent article as defined in claim 28, wherein the adhesive is applied in varying amounts in order to control stretch properties of the chassis in the lateral direction.

33. An absorbent article as defined in claim 20, wherein the outer cover comprises an elastic laminate containing a nonwoven web.

34. An absorbent article as defined in claim 20, wherein the liner comprises a liquid permeable elastic film or a nonwoven web containing an elastic material.

35. An absorbent article as defined in claim 20, wherein the outer cover and the bodyside liner are continuous from the first edge zones to the second edge zones.

36. An absorbent article comprising:

an elastic outer cover;

an elastic bodyside liner joined to the elastic outer cover in a superimposed relation;

an absorbent structure positioned in between the outer cover and the liner;

wherein the outer cover, liner and absorbent structure form a chassis, the chassis including a front region and a back region that define a waist opening therebetween opposite two leg openings when worn about a wearer, the chassis comprising three equal distant zones in a lateral direction along the widest portion of the front region and along the widest portion of the back region of the chassis, the zones of the front region and the back region including a first edge zone, a middle zone, and a second edge zone, and wherein the chassis is constructed such that the chassis has a total stretch of from about 25% to about 150% along the widest portion of the front region and along the widest portion of the back region when at a tension of 100 g/cm; and wherein the absorbent structure is attached to the liner, to the outer cover or to both the liner and the outer cover in a manner that inhibits stretch of the chassis within the middle zones such that at least about 70% of the total stretch contained along the widest portion of the front region is contained within the respective first and second edge zones and wherein at least about 70% of the total stretch contained along the widest portion of the back region is also contained in the respective first and second edge zones.

37. An absorbent article as defined in claim 36, wherein the absorbent structure is substantially non-elastic.

38. An absorbent article as defined in claim 36, wherein at least about 90% of the total stretch in the widest portion of the front region is contained in the respective first and second edge zones and wherein at least about 90% of the total stretch contained along the widest portion of the back region is also contained in the respective first and second edge zones.

39. An absorbent article as defined in claim 36, wherein the absorbent structure is attached to the liner, the outer cover or to both the liner and the outer cover using an adhesive.

40. An absorbent article as defined in claim 39, wherein the adhesive comprises a hot melt adhesive.

41. An absorbent article as defined in claim 36, wherein the absorbent structure is attached to the liner, the outer cover or to both the liner and the outer cover using ultrasonic bonding or thermal bonding.

42. An absorbent article as defined in claim 39, wherein the adhesive is applied in varying amounts in order to control the stretch properties of the chassis in the lateral direction.

43. An absorbent article as defined in claim 36, wherein the outer cover comprises an elastic laminate containing a nonwoven web.

44. An absorbent article as defined in claim 36, wherein the liner comprises a liquid permeable elastic film or a nonwoven web containing an elastic material.

45. An absorbent article as defined in claim 36, wherein the middle zone of the front region and the middle zone of the back region have substantially no stretch when placed under lower lateral tensions, at tensions greater than about 80 g/cm, however, the attachment of the absorbent structure to the chassis at least partially breaks down releasing stretch within the middle zones of the front region and the back region.

* * * * *